United States Patent [19]
Brush et al.

[11] Patent Number: 5,986,086
[45] Date of Patent: Nov. 16, 1999

[54] NON-SULFONATED CYANINE DYES FOR LABELING NUCLEOSIDES AND NUCLEOTIDES

[75] Inventors: Charles K. Brush, Whitefish Bay; Ned D. Reimer, West Allis, both of Wis.

[73] Assignee: Amersham Pharmacia Biotech Inc., Piscataway, N.J.

[21] Appl. No.: 08/879,596

[22] Filed: Jun. 20, 1997

[51] Int. Cl.$^6$ .................................................. C07H 19/04
[52] U.S. Cl. .................. 536/26.26; 536/25.3; 536/25.31; 536/25.32; 536/26.7; 548/416; 548/455; 435/6
[58] Field of Search .................................. 536/25.3, 26.7, 536/25.31, 25.32, 25.34, 25.4, 25.41, 26.6, 26.8, 28.53, 28.54, 26.71, 27.8, 27.81; 548/416, 455; 435/6

[56] References Cited

U.S. PATENT DOCUMENTS

| | | |
|---|---|---|
| 4,981,977 | 1/1991 | Southwick et al. . |
| 5,268,486 | 12/1993 | Waggoner et al. . |
| 5,556,959 | 9/1996 | Brush et al. . |
| 5,569,587 | 10/1996 | Waggoner . |
| 5,627,027 | 5/1997 | Waggoner . |

FOREIGN PATENT DOCUMENTS

| | | |
|---|---|---|
| WO 91/17169 | 11/1991 | WIPO . |
| WO 95/04747 | 2/1995 | WIPO . |
| WO 96/22298 | 7/1996 | WIPO . |

OTHER PUBLICATIONS

J.B. Randolph and A.S. Waggoner, "Stability, Specificity and Fluorescence Brightness of Multiply–labeled Fluorescent DNA Probes," *Nuc. Acids Res.* 25(14):2923–2929, 1997.

Z. Zhu, et al., "Directly Labeled DNA Probes Using Fluorescent Nucleotides with Different Length Linkers," *Nuc. Acids Res.* 22(16):3418–3422, 1994.

E. Anderson, et al., "Synthesis of a Carbocyanine Phsophoramidite and its use in Oligonucleotide Labeling," International Conference on Nucleic Acid Medical Applications, Jan. 15, 1993.

D. Andrews–Wilberforce and G. Patonay, "Fluorescence Quenching Studies of Near–Infrared Fluorophores," *App. Spectro.* 43(8):1450–1455, 1989.

Collaborative Research, Semiannual Progress Report No. 2, 1978.

B.H. Dahl, et al., "Mechanistic Studies on the Phosphoramidite Coupling Reaction in Oligonucleotide Synthesis. I. Evidence for Nucleophilic Catalysis by Tetrazole and Rate Variations with the Phosphorus Substituents," *Nucl. Acids Res.* 15(4):1729–1743, 1987.

J.H. Kenton, et al., "Improved Electrochemiluminescent Label for DNA Probe Assays: Rapid Quantitative Assays of HIV–1 Polymerase Chain Reaction Products," *Clin. Chem.* 38(6):873–879, 1992.

M. Mag and J.W. Engels, "Synthesis and Selective Cleavage of Oligodeoxyribonucleotides Containing Non–chiral Internucleotide Phosphoramidate Linkages," 17(15):5973–5988.

R.B. Mujumdar, et al., "Cyanine Dye Labeling Reagents Containing Isothiocyanate Groups," *Cytometry* 10:11–19, 1989.

Nippon Zeon, JP 62070391, 1987 (Abstract).

K.K. Ogilvie, et al., "Total Chemical Synthesis of a 77–nucleotide–long RNA Sequence having Methionine–acceptance Activity," *Proc. Natl. Acad. Sci. USA* 85:5764–5768, 1988.

G. Patonay and M.D. Antoine, "Near–infrared Fluorogenic Labels: New Approach to an Old Problem," *Analy. Chem.* 63(6):321–326, 1991.

J.C. Schulhof, et al., "The Final Deprotection Step in Oligonucleotide Synthesis is Reduced to a Mild and Rapid Ammonia Treatment by using Labile Base–protecting Groups," *Nucl. Acids Res.* 15(2):397–416, 1987.

Sekine, et al., *J. Am. Chem. Soc.* 108:4581–4586, 1986.

H. Seliger and H.–H. Görtz, "Kenetik der Schutzgruppenabspaltung bei Derivaten des 2'–Desoxycytiden–5'–phosphats," *Chem. Ber.* 111:3732–3739, 1978.

P.L. Southwick, et al., "Cyanine Dye Labeling Reagents— Carboxymethylindocyanine Succinimidyl Esters," *Cytometry* 11:418–430, 1990.

H. Yu, et al., "Cyanine Dye dUTP Analogs for Enzymatic Labeling of DNA Probes," *Nucl. Acids Res.* 22(15):3226–3232, 1994.

H. Yu, et al., "Sensitive Detection of RNAs in Single Cells by Flow Cytometry," *Nucl. Acids Res.* 20(1):83–88, 1991.

*Primary Examiner*—James O. Wilson
*Attorney, Agent, or Firm*—Quarles & Brady LLP

[57] ABSTRACT

A chemical compound of the following formula:

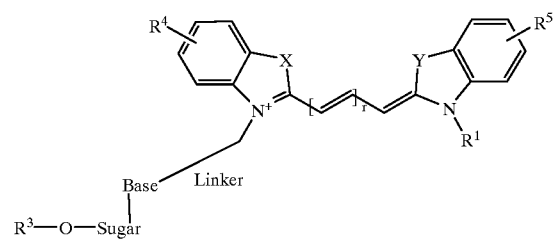

wherein $R^1$ is selected from the group consisting of alkyl, aralkyl, and substituted alkyl groups; $R^3$ is selected from the group consisting of H, $PO_3^{-2}$, $P_2O_6^{-3}$; $P_3O_9^{-4}$, and α-thio phoshates ($PSO_2^{-2}$; $P_2SO_5^{-3}$; $P_3O_8^{-4}$); and $\alpha BH_3^-$ phosphates ($P(BH_3)O_2^{-2}$, $P_2(BH_3)O_5^{-3}$, $P_3(BH_3)O_8^{-4}$); $R^4$ is selected from the group consisting of H, lower alkyl, acyl, $(CH_2)_pCOO(CH_2)_qCH_3$ wherein p is an integer from 0 to 4 and q is an integer from 0 to 4, and 5,6; 6,7; or 7,8-butadienyl; $R^5$ is selected from the group consisting of H lower alkyl, acyl, $(CH_2)_pCOO(CH_2)_qCH_3$ wherein p is an integer from 0 to 4 and q is an integer from 0 to 4 and 5,6; 6,7; or 7,8- butadienyl; r is 1, 2, or 3 to form a second fused aromatic; X or Y are selected from the group consisting of O, S, $C(R^6)_2$, or $N(R_6)$, wherein $R^6$ is preferably $CH_3$ or a lower alkyl; and $R^3$—O-Sugar-Base is a nucleoside or nucleotide is disclosed.

14 Claims, 6 Drawing Sheets

INTERMEDIATE FROM
AMIDITE AYNTHESIS

TWO ALTERNATIVE LINKERS

NON-SULFONATED CYANINE DYES FOR LABELING NUCLEOSIDES AND NUCLEOTIDES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Cyanine dyes have been described in the literature for many years[1,2], mainly for photographic purposes. In recent years, researchers have taken advantage of the excellent fluorescent properties of the carbocyanines to label biological molecules. Initial efforts were thwarted by the high background and/or quenching of fluorescence observed when the dyes were conjugated to proteins. The hydrophobic nature of the dyes caused them to aggregate in aqueous media or on the hydrophobic domains of proteins. Thus, the dyes, as described in the early literature, were not suitable for labeling.

Waggoner, et al.[3,4] disclosed the use of sulfonated derivatives of carbocyanines to label biological molecules. The sulfonate group was found to be effective at preventing aggregation, because of the repulsion of the negative charges between molecules. In some of the cited Waggoner disclosures, the importance of the sulfonate groups to the novelty and efficacy of the dye derivatives, which included nucleic acids, was emphasized.

U.S. Pat. No. 5,556,959 discloses the use of carbocyanine phosphoramidites to label synthetic oligonucleotides. Due to the constraints of the automated systems used for DNA synthesis, the amidites had to be soluble in aprotic organic solvents. Sulfonated carbocyanines are insoluble in the solvents best suited for oligonucleotide synthesis. Therefore, the dye amidites described in U.S. Pat. No. 5,556,959 lacked the sulfonate groups. Experiments showed that the amidites were soluble in the appropriate solvents, such as acetonitrile and dichloromethane, and labeled the oligonucleotides in high yield. The dye amidites and intermediates are easily and efficiently synthesized and purified.

Nucleoside triphosphates (NTPs) labeled with reporter groups have been in use for many years[5,6]. NTPs labeled with sulfonated carbocyanines have been reported in the scientific literature[7a], and are commercially available[7b]. However, synthesis of sulfonated cyanines is a difficult procedure, and the purity of the dye intermediates used in labeling is variable. The recommended shelf-life is short. Reagents for labeling are therefore expensive, as are the labeled NTPs derived from them.

Needed in the art of molecular biology is a nonsulfonated cyanine dye attached to a nucleotide or nucleoside.

BRIEF SUMMARY OF THE INVENTION

The present invention is a chemical compound of the following formula:

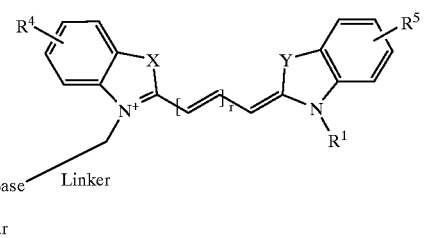

wherein $R^1$ is selected from the group consisting of alkyl, aralkyl, and substituted alkyl. Preferable $R^1$ substitutions include, but are not limited to, $OR^2$, $COOR^2$, $NR^2R^2$, $SR^2$, most preferably where $R^2$ is H, a removable protecting group, or a lower alkyl group. $R^3$ is H, $PO_3^{-2}$; $P_2O_6^{-3}$; $P_3O_9^{-4}$; α-thio phosphates, such as $PSO_2^{-2}$; $P_2SO_5^{-3}$; $P_3SO_8^{-4}$; and $\alpha BH_3^-$ phosphates, such as $P(BH_3)O_2^{-2}$; $P_2(BH_3)O_5^{-3}$; $P_3(BH_3)O_8^{-4}$. $R^4$ is selected from the group consisting of H, lower alkyl, acyl, and $(CH_2)_p COO(CH_2)_q CH_3$, wherein p is an integer from 0 to 4 and q is an integer from 0 to 4. $R^5$ is selected from the group consisting of H, lower alkyl, acyl, and $(CH_2)_p COO(CH_2)_q CH_3$ wherein p is an integer from 0 to 4 and q is an integer from 0 to 4. $R^4$ or $R^5$ may also be 5,6; 6,7; or 7,8-butadienyl (thus forming a second fused aromatic ring). r is 1, 2, or 3 and X and Y are O, S, $C(R^6)_2$, $N(R^6)$ (wherein $R^6$ is preferably $CH_3$ or a lower alkyl). $R^3$—O-Sugar-Base is a nucleotide or nucleoside.

It is an object of the present invention to provide a nucleotide or nucleoside attached to a nonsulfonated cyanine dye.

It is another object of this present invention to provide a nucleoside or nucleotide attached to a fluorescent label.

Other objects, advantages, and features of the present invention will become apparent after one has examined the specification, claims, and drawings of the present invention.

DETAILED DESCRIPTION OF THE INVENTION

The present invention is a chemical compound of the general formula

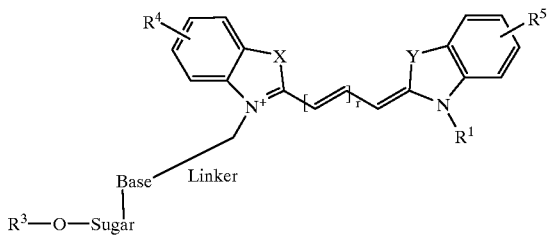

$R^1$ is selected from the group consisting of alkyl, aralkyl, and substituted alkyl chains. Preferably, the substitutions are $OR^2$, $COOR^2$, $NR^2R^2$, $SR^2$, where $R^2$ is preferably H, a removable protecting group such as trityl or acetyl, or a lower alkyl group (n=1–4). In the examples below, we describe a compound of the present invention in which R is $(CH_2)_3OH$. Other preferred R groups are $(CH_2)_5COOH$, $(CH_2)_3NH_2$, and $C_2H_5$.

$R^3$ is either H, $PO_3^{-2}$, $P_2O_6^{-3}$, $P_3O_9^{-4}$, α-thio phosphates, such as $PSO_2^{-3}$, $P_2SO_5^{-3}$, $P_3SO_8^{-4}$, and $αBH_3^-$ phosphates, such as $P(BH_3)O_2^{-2}$, $P_2(BH_3)O_5^{-3}$, or $P_3(BH_3)O_8^{-4}$.

$R^4$ is selected from the group consisting of H, lower alkyl, acyl, and $(CH_2)_pCOO(CH_2)_qCH_3$, wherein p is an integer from 0 to 4 and q is an integer from 0 to 4. $R^5$ is selected from the group consisting of H, lower alkyl, acyl, and $(CH_2)_pCOO(CH_2)_qCH_3$ wherein p is an integer from 0 to 4 and q is an integer from 0 to 4. $R^4$ or $R^5$ may also be 5,6; 6,7; or 7,8- butadienyl (thus forming a second fused aromatic ring). r is 1, 2, or 3 and X and Y are O, S, $C(R^6)_2$, $NR^6$, wherein $R^6$ is preferably $CH_3$ or a lower alkyl (n=1–4), such as $CH_2CH_3$.

The butadienyl compounds are disclosed in 08/799,593 filed Feb. 10, 1997, by Brush and Anderson, which hereby is incorporated by reference.

Figure 4:
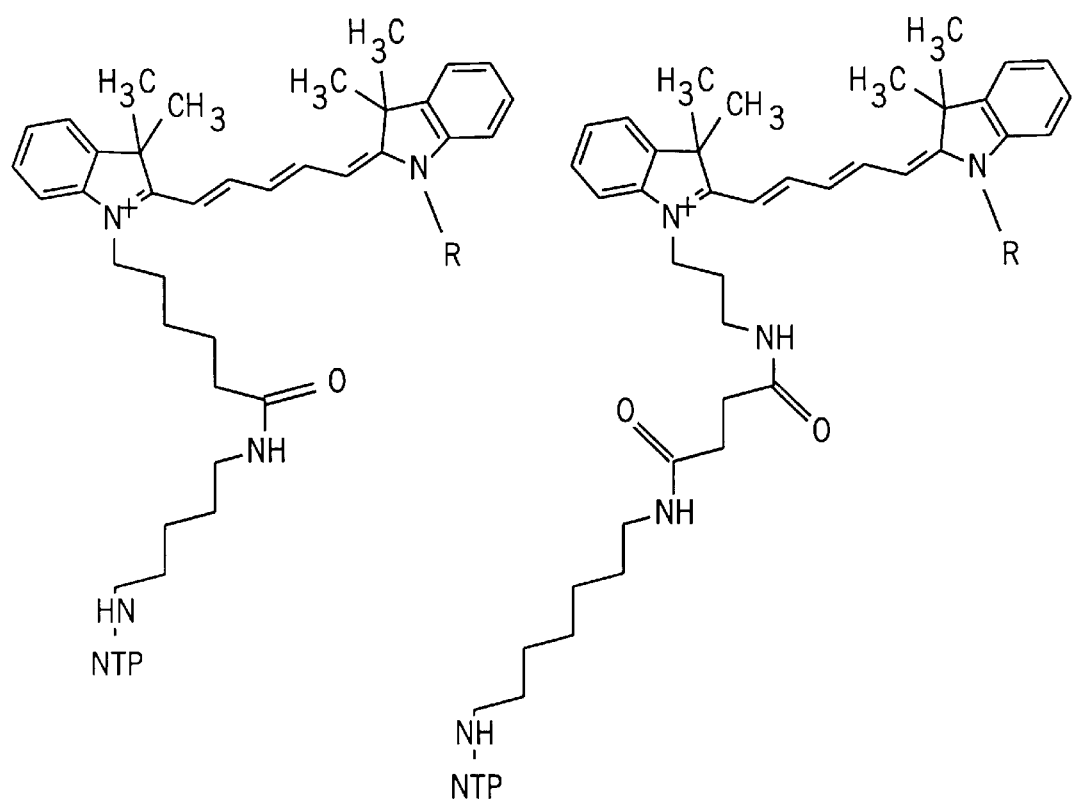
FIG. 4 is a diagram of alternative linkers.

"Linker" is a combination of carbon, oxygen, nitrogen, and/or sulfur atoms in a chain that connects the dye through N1 to a position on the base. The linker may contain amide, ester, urea, thiourea, amine, ether, sulfide or disulfide bonds. The position on the base may be $C^5$ or $C^6$ of uracil, $C^6$ of thymine, $N^4$, $C^5$, or $C^6$ of cytosine, $N^2$, $N^7$, or $C^8$ of guanine, $N^2$, $C^7$, or $C^8$ of 7-deazaguanine, $C^8$ of hypoxanthine, $C^7$ or $C^8$ of 7-deazahypoxanthine, $N^6$ or $C^8$ of adenine, or $N^6$, $C^7$, or $C^8$ of 7-deazaadenine. Preferable linkers are listed below in the Examples (for example, propyl-O—$PO_2$—O-hexyl, propyl-$O_2$C-ethyl-CO, propyl-$O_2$C-ethyl-CONH-hexyl, and propyl-$O_2$C-ethyl-CONH-propynyl) and in FIG. 4. Preferable linkers are between 3 and 25 atoms in length.

Base, sugar and $R^3$ combine to form nucleotides and nucleosides known to one of skill in the art.

"Base" may be uracil, thymine, cytosine, guanine, 7-deazaguanine, hypoxanthine, 7-deazahypoxanthine, adenine, or 7-deazaadenine, 2,6-diaminopurine or other nitrogen-heterocycle bases, such as those described in reference 8 and references therein.

"Sugar" may be ribosyl, 2'-deoxyribosyl, 3'-deoxyribosyl, or 2',3'-dideoxyribosyl or 2'-oxabutyl, the sugar being preferably attached at N1 to the pyrimidines, and N9 to the purines and deazapurines.

"$R^3$—O-Sugar-Base" indicates that the $R^3$ group is preferably attached to the 5' oxygen of the sugar. In the case of the 2-oxabutyl "sugar," there is no 5' oxygen and the $R^3$ group would be attached to the 4' oxygen.

The Examples below disclose preferred methods of synthesis of the compound of the present invention.

In general, the synthesis of the compounds may be described as follows: The aromatic quaternary ammonium salt is prepared by alkylation of a 2-methyl indolenine, benzoxazole, or benzthiazole, or related benzo derivative. The alkylating agent contains a (protected) functional group which may be further derivatized. Two molecules of the resulting quaternary salt are condensed with one molecule of a protected unsaturated dialdehyde to yield a symmetrical cyanine. Alternatively, one molecule is condensed with a di-anil of an unsaturated dialdehyde. The product is then condensed with a different aromatic quaternary ammonium salt to give an unsymmetrical cyanine.

The functional group on the alkylating agent is then deprotected (if necessary) and derivatized to yield an activated group which is capable of reacting with a group on the nucleoside triphosphate. Many methods are known to the art which can be adapted to accomplish this.

The present invention is also a method of labelling a nucleic acid. Preferably, one would incorporate the compound described above into the nucleic acid chain in the same manner that one incorporates other nucleotides. In a most preferable form of the invention, one would then determine the nucleic acid sequence of the labelled nucleic acid molecule.

EXAMPLES

In General

The reaction schemes described below are general for several of the compounds made by the method. "NTP" signifies a nucleoside, or nucleoside mono-, di-, or triphosphate, bound through an amino group to the linker and dye. All the synthesized examples are triphosphates, as they are the most difficult, but also most useful, compounds to prepare.

The following abbreviations are used:

TABLE 1

|  | r = | X = |
|---|---|---|
| IMC = indomonocarbocyanine | 1 | $C(CH_3)_2$ |
| IDC = indodicarbocyanine | 2 | $C(CH_3)_2$ |
| ITC = indotricarbocyanine | 3 | $C(CH_3)_2$ |
| BMC = benz(e)indomonocarbocyanine | 1 | $C(CH_3)_2$ |
| BDC = benz(e)indodicarbocyanine | 2 | $C(CH_3)_2$ |
| BTC = benz(e)indotricarbocyanine | 3 | $C(CH_3)_2$ |
| OMC = benzoxazolemonocarbocyanine | 1 | O |
| ODC = benzoxazoledicarbocyanine | 2 | O |
| OTC = benzoxazoletricarbocyanine | 3 | O |
| TMC = benzthiazolemonocarbocyanine | 1 | S |
| TDC = benzthiazoledicarbocyanine | 2 | S |
| TTC = benzthiazoletricarbocyanine | 3 | S |
| NOMC = naphthoxazolemonocarbocyanine | 1 | O |
| NODC = naphthoxazoledicarbocyanine | 2 | O |
| NOTC = naphthoxazoletricarbocyanine | 3 | O |
| NTMC = naphththiazolemonocarbocyanine | 1 | S |
| NTDC = naphththiazoledicarbocyanine | 2 | S |
| NTTC = naphththiazoletricarbocyanine | 3 | S |

| Nucleoside | mono-phos | di-phos | tri-phos |
|---|---|---|---|
| A = adenine | (none) | (none) | (none) |
| rA = adenosine (ribo) | AMP | ADP | ATP |
| dA = 2'-deoxyadenosine | dAMP | dADP | dATP |
| ddA = 2',3'-dideoxyadenosine | ddAMP | ddADP | ddATP |
| aA = Acyclo (2 oxabutyl) | aAMP | aADP | aATP |

Similarly, C = cytosine, cytidine; G = guanine, guanosine; $c^7$-G = 7-deazaguanine T = thymine, thymidine; U = uracil, uridine Compounds prepared by the method described in FIG. 2 include:

IDC-rCTP

IDC-dCTP

IDC-ddCTP

ITC-ddCTP

ITC-ddATP
IDC-DATP
IMC-c7-ddGTP
OMC-ddCTP
IMC-ddCTP

A study using visible spectroscopy was done to determine whether the hydrophobic dyes aggregate in aqueous solution. The greater the shorter wavelength shoulder, the more aggregation is occurring. The concentration of indotricarbocyanine-ddATP, one of the most hydrophobic dye-nucleoside conjugates, was varied over a range from 0.6 to 80 µM. The ratio of 744 nm 682 nm was observed (the wavelength maximum to the shorter wavelength at the shoulder of ITC spectrum). Variation was approximately ±5% over the entire range, compared to the ratio at a median absorption of $A_{744}$=0.578: $A_{682}$=0.202, indicating very little, if any aggregation.

Experimental Procedures

Example 1

Figure 5:
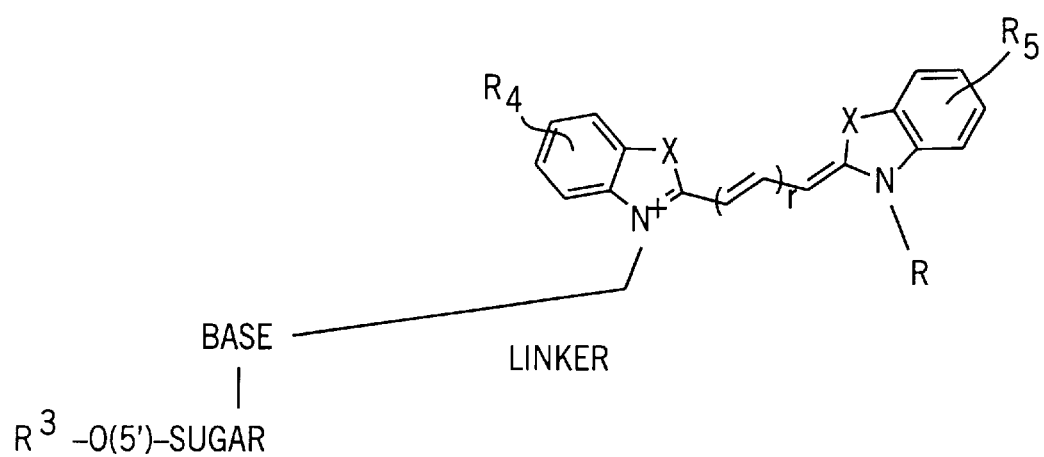
FIG. 5 is a diagram of the general formula of the present invention.

(FIG. 5, r=2, X=C(CH$_3$)$_2$, $R^4$=$R^5$=H, R=(CH$_2$)$_3$OH, $R^3$=5'-O-triphosphate, linker=DYE-(propyl-O—PO$_2$—O—hexyl)-BASE; sugar=deoxyribosyl; base=adenine-$N^6$.)

1-3"-($N^6$-hexyldeoxyadenosine, 5'-O-triphosphate)-propyl)phosphate)-1'-(3"'-hydroxypropyl)-3,3,3',3'-tetramethyl-indodicarbocyanine (β-Cyanoethyl)

(1-(3"'-(1"'-propyl))-1'-(3"-(1"-(p-methoxytrityl) oxypropyl))-3,3,3',3'-tetramethyl-indodicarbocyanine) (6-N-trifluoroacetylaminohexyl) phosphate The mono MMTr intermediate for the preparation of the corresponding amidite (1.13 g, 0.00145 mol), was treated with 6-N-trifluoroacetylaminohexyl-β-cyanoethyl-N,N-diisopropylamino-phosphoramidite (1.4 g, 0.0065 mol) and 0.4 g (0.0056 mol) of tetrazole (in 2 mL of dry acetonitrile) in 7 mL of dry dichloromethane. The reaction was stirred overnight, and then treated with 10 mL of 0.35 M iodine in a mixture of pyridine, water, and collidine. The solution was diluted with dichloromethane and extracted with aqueous bicarbonate and brine. The solution was dried and evaporated to leave the fully protected phosphotriester.

(1-(3"'-(1"'-propyl)-1'-(3"-oxypropyl))-3,3,3',3'-tetramethyl-indodicarbocyanine) (6-aminohexyl) phosphate The triester was dissolved in 50 mL of ethanol, to which 150 mL or 3:1 conc. ammonia/ethanol were added. After two hours at 60° C., the TFA and cyanoethyl protecting groups had been removed. The solvents were evaporated and the residue was dissolved in 50 mL of 7% trichloroacetic acid for one hour. The reaction mixture was neutralized by extraction with aqueous bicarbonate, dried, and evaporated. The residue was purified by C-18 NovaPak column chromatography with a 15 minute gradient of 40–100% acetonitrile in triethylammonium acetate, 0.1 M, pH 7.0. $R_f$=7.8 minutes. The isolated material had the expected UV/visible spectrum, λ=648 nm.

(1-(3"'-(1"'-propyl)-1'-(3"-oxypropyl))-3,3,3',3'-tetramethyl-indodicarbocyanine) (6-aminohexyl $N^6$-deoxyadenosine, 5'-O-triphosphate) phosphate The aminohexyl-derivatized dye above was dissolved in 500 µL of 0.1 M sodium borate, pH 9.2. To this was added 6-chloropurine-9-(1'-β-deoxyriboside-5'-O-triphosphate). The reaction was stirred overnight at 60° C., after which time HPLC (C-18, 0–70% acetonitrile/TEAA) analysis showed a high percentage of the product. The main peak was isolated by prep C-18 HPLC, 10–50% acetonitrile/0.05 M ammonium phosphate, pH 7.2 over a 40 minute gradient. It was repurified twice by prep C-18 HPLC, 15–40% acetonitrile/0.05 M ammonium phosphate, pH 7.2 over a 40 minute gradient to a purity of >99%. The product was desalted on a C-18 cartridge and stored in aqueous solution. The UV/visible spectrum showed the expected peaks at 648 nm for the dye and 268 nm for an $N^6$-derivatized adenine.

The material was compared with Cy5-29$^{TM}$-dATP, prepared by reaction of commercially obtained Cy5-29$^{TM}$-OSu (NHS ester) with $N^6$-aminohexyl-dATP. The UV/visible spectra were identical, and the automated sequencing results obtained on ALFexpress (Pharmacia Biotech) were comparable. The sequencing results demonstrate that there is no difference in the reaction of the unsulfonated material described here, and the Cy5$^{TM}$-29-labeled material, which bears two sulfonate groups.

Example 2

(FIG. 5, r=2, X=C(CH$_3$)$_2$, $R^4$=$R^5$=H, R=(CH$_2$)$_3$OH, $R^3$=5'-O-triphosphate, linker=DYE-(propyl-O$_2$C-ethyl-CO)-BASE; sugar=deoxyribosyl; base=cytosine-$N^4$.)

Figure 3:
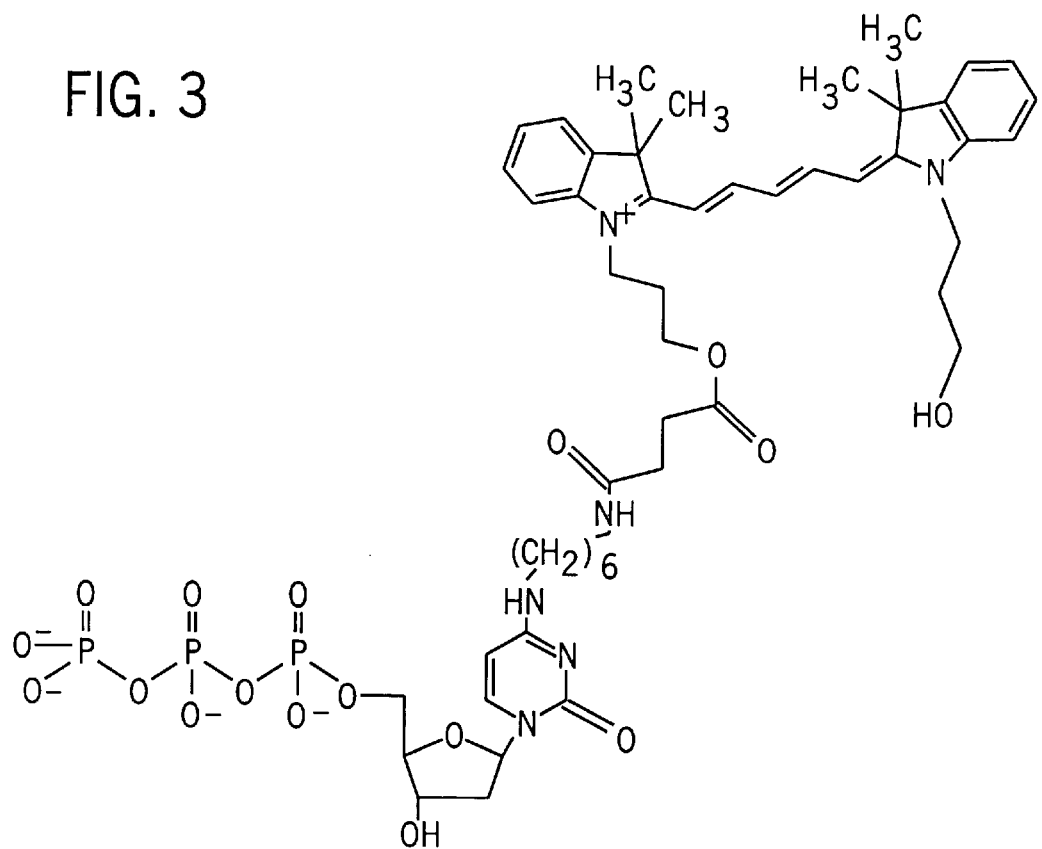
FIG. 3 is a diagram of indodicarbocyanine (IDC)-dCTP.

1-3"-($N^4$-6-amidohexyldeoxycytidine-5'-O-triphosphate)-succinoyloxypropyl)-1'-(3"'-hydroxypropyl))-3,3,3',3'-tetramethyl-indodicarbocyanine (See FIG. 3)

(1-(3"'-(1"'-Propyloxysuccinic acid))-1'-(3"-(1"-(p-methoxytrityl) oxypropyl))-3,3,3',3'-tetramethyl-indodicarbocyanine)

The mono MMTr intermediate for the preparation of the amidite (1 g, 0.00128 mol), was dissolved in 10 mL of pyridine and treated with 0.384 g (0.004 mol) succinic anhydride and 0.11 g 4-dimethylaminopyridine (0.0058 mol). The reaction was stirred for 4 hours at ambient temperature. Progress was monitored by C-18 HPLC on a 3 µm column at 80% acetonitrile/TEAA, isocratic, detected at 648 nm. After the addition of 1 mL of water, the reaction was evaporated to dryness. The residue was dissolved in dichloromethane and was extracted with aqueous bicarbonate and brine. After drying, the organic layer was evaporated to dryness.

(1-(3"'-(1"'-Propyloxysuccinic acid))-1'-(3"-(1"-hydroxypropyl))-3,3,3',3'-tetramethyl-indodicarbocyanine)

The material from the previous reaction was dissolved in 30 mL of 80% acetic acid in water. After five hours at ambient temperature, the detritylation was complete, with no hydrolysis of the succinate ester. Progress was monitored by C-18 HPLC on a 3 µm column at 50% acetonitrile/TEAA, isocratic for 1 minute, then to 100% acetonitrile in 10 minutes, detected at 648 nm. The solution was evaporated and the residue dissolved in dichloromethane, extracted with aqueous bicarbonate three times, and brine. The solution was dried and evaporated to a blue powder.

(1-(3"'-(1"'-Propyloxysuccinic acid, N-hydroxysuccinimide ester))-1'-(3"-(1"-hydroxypropyl))-3,3,3',3'-tetramethyl-indodicarbocyanine)

The dry solid was dissolved in 10 mL of dry dichloromethane, followed by 0.5 mL pyridine and 0.81 g (~3 eq) of O-trifluoroacetyl-N-hydroxysuccinimide. The reaction, monitored by C-18 HPLC on a 3 µm column at 50% acetonitrile/TEAA, isocratic for 1 minute, then to 100% acetonitrile in 10 minutes, detected at 648 nm, was over in 5 minutes. Dichloromethane was added to 30 mL and the solution was extracted with water three times, dried, and evaporated.

1-3"-(N⁴-6-Amidohexyldeoxycytidine-5'-O-triphosphate)-succinoyloxypropyl)-1'-(3'"-hydroxypropyl))-3,3,3',3'-tetramethyl-indodicarbocyanine N⁴-(6-Aminohexyl)-dCTP was dissolved in 0.3 mL of 0.1 M sodium carbonate, pH 9.4. To this was added 200 µL of DMF, followed by 100 µL of DMF containing 10 mg of the aminolinker dye. The pH was readjusted to 9.4. The reaction was stirred for 1.5 hours at ambient temperature, at which time anion exchange HPLC (5–50% B in A over 30 minutes; A=0.005 M sodium phosphate, pH 7.5 with 20% acetonitrile; B=A+1 M NaCl) analysis showed a high percentage of the product at ~6 minutes. The main peak was repurified by C-18 HPLC, 5% for 2 minutes, then 5–60% acetonitrile/0.05 M ammonium phosphate, pH 7.2 over a 40 minute gradient. It was repurified twice prep C-18 HPLC, 15–40% acetonitrile/0.05 M ammonium phosphate, pH 7.2 over a 40 minute gradient to a purity of >99%. The product was desalted on a C-18 cartridge and stored in aqueous solution. The UV/visible spectrum showed the expected peaks at 648 nm for the dye and 276 nm for an N⁴-derivatized cytosine.

The material was compared with Cy5-29$^{TM}$-dCTP, prepared by reaction of commercially obtained Cy5-29$^{TM}$-OSu (NHS ester) with N⁴-aminohexyl-dCTP. The UV/visible spectra were identical, and the sequencing results obtained on ALFexpress (Pharmacia Biotech) were comparable. The sequencing results demonstrate that there is no difference in the reaction of the unsulfonated material described here, and the Cy5$^{TM}$-29-labeled material, which bears two sulfonate groups.

Example 3

(FIG. 5, r=2, X=C(CH₃)₂, R⁴=R⁵=H, R=(CH₂)₃OH, R³=5'-O-triphosphate, linker=DYE-(propyl-O₂C-ethyl-CONH-hexyl)-BASE; sugar=ribosyl; base=cytosine-N⁴.)

Figure 1A:
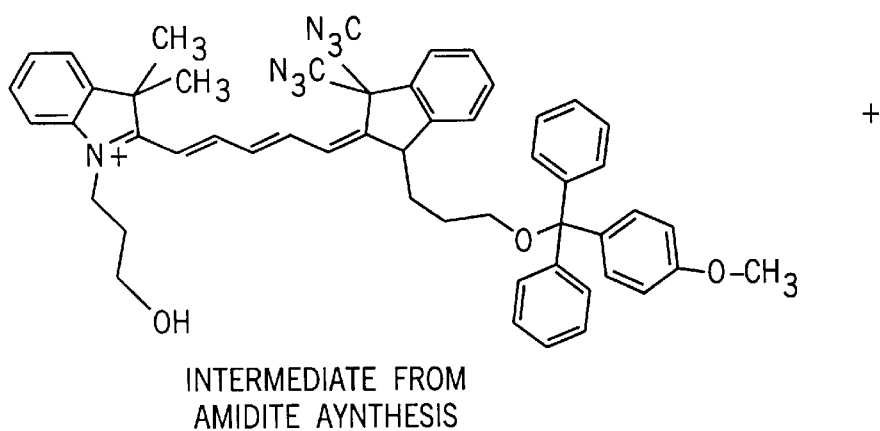
FIG. 1 is a schematic diagram of the synthesis of a cyanine dye-linked nucleoside originating with an amidite synthesis intermediate.
Figure 1A:
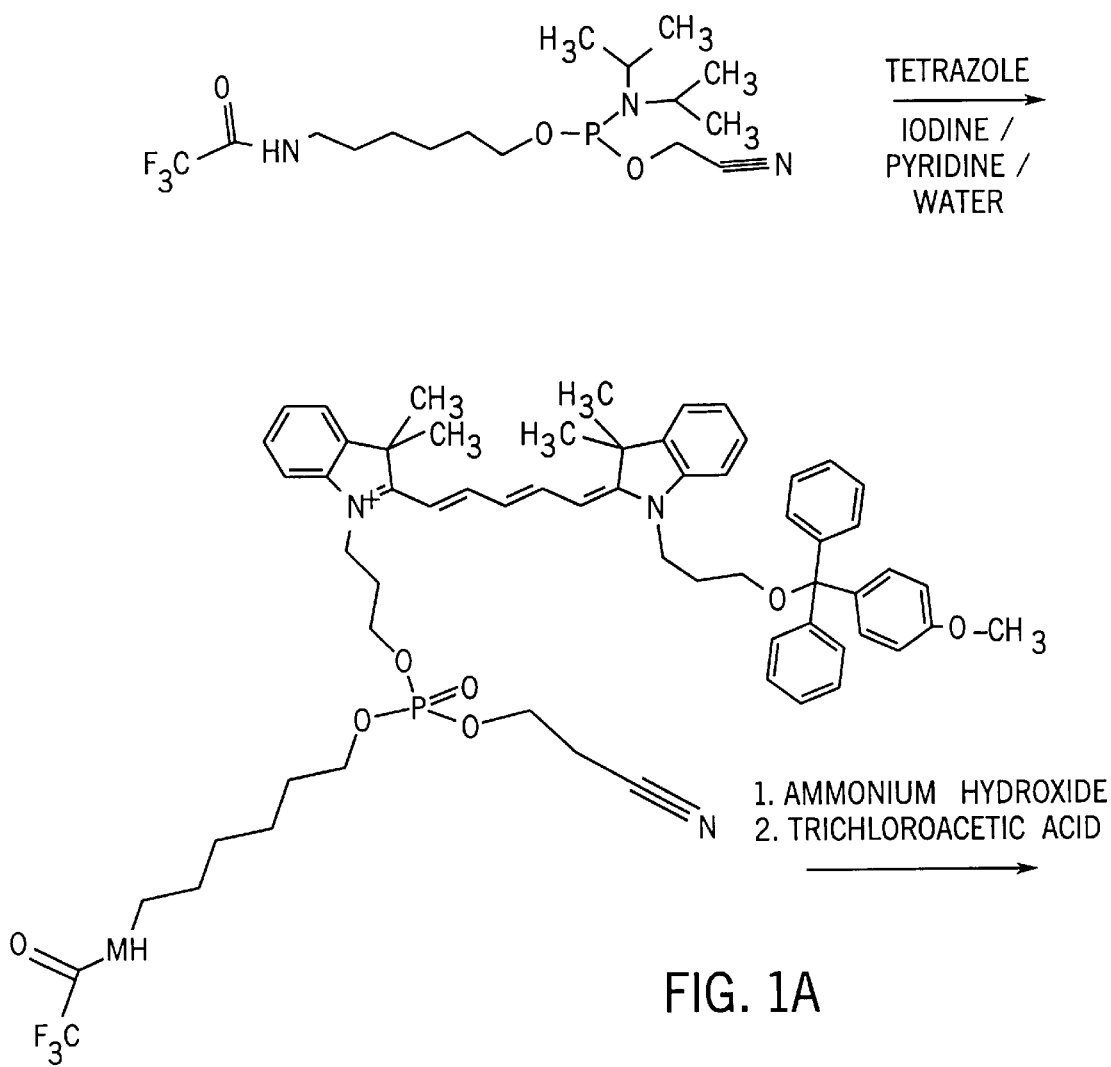
Figure 1B:
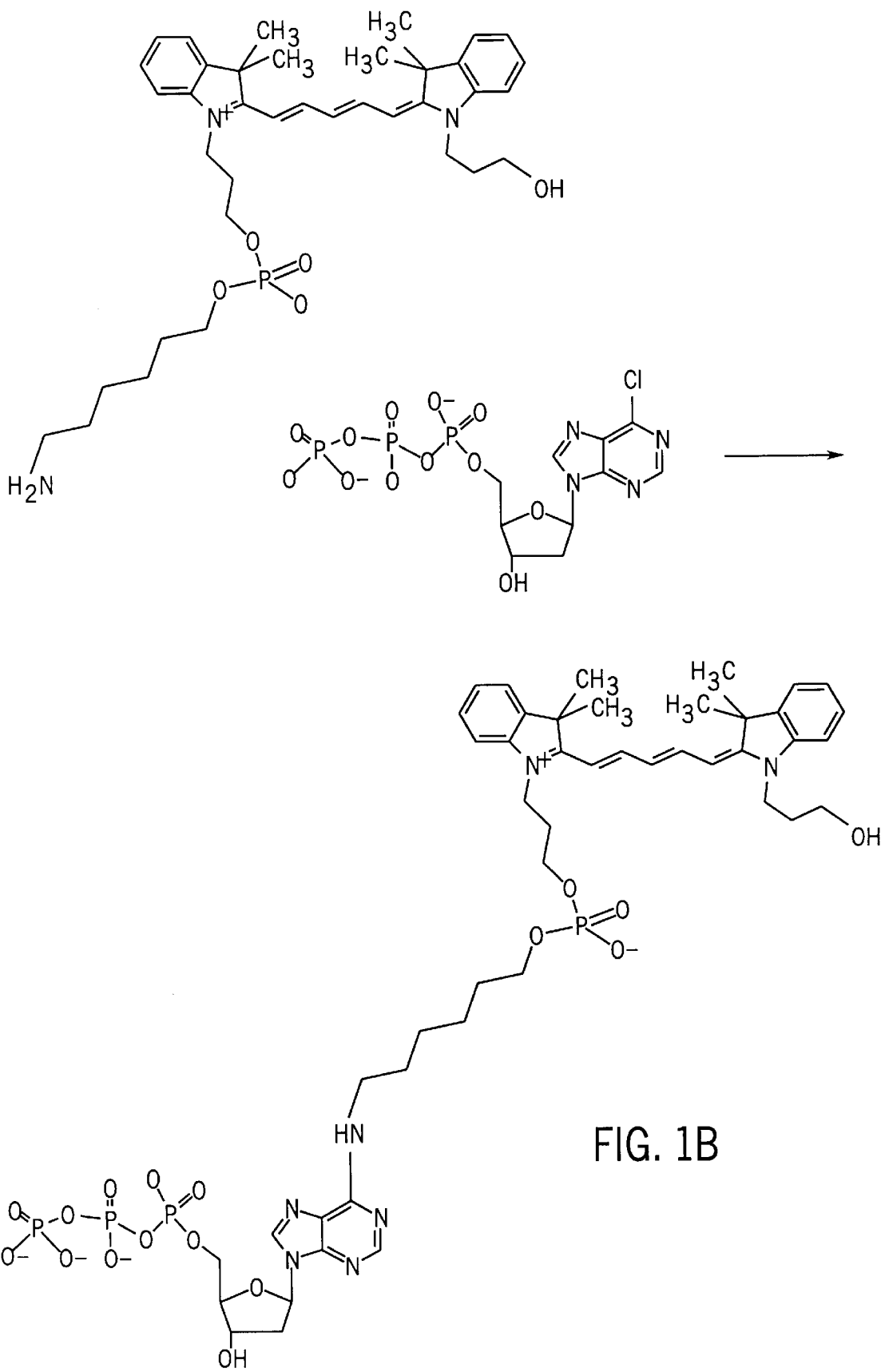
Figure 2:
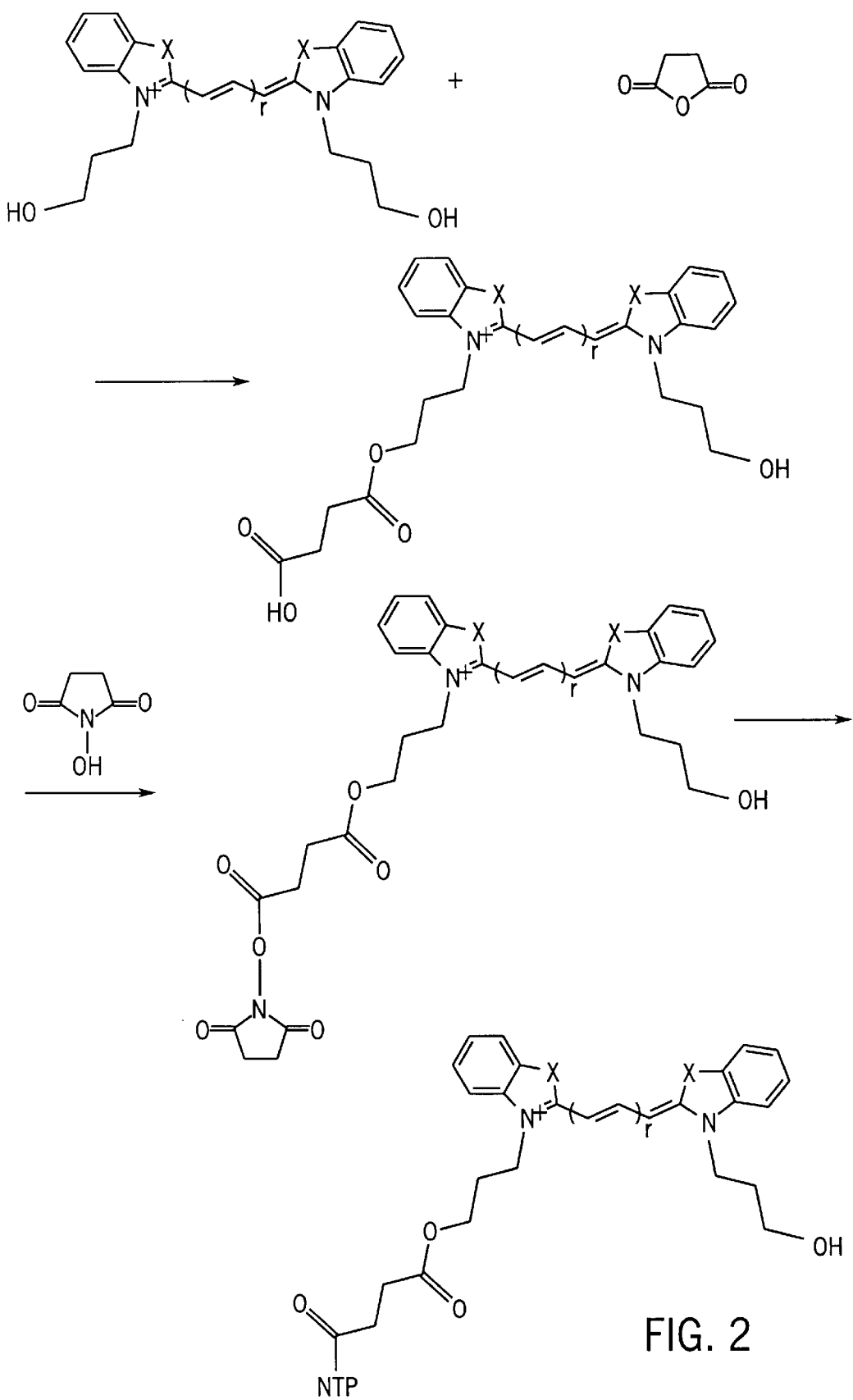
FIG. 2 is a schematic diagram of the synthesis of a cyanine dye-linked nucleotide.

1-3"-((N⁴-6-Amidohexylcytidine, 5'-O-triphosphate)-succinoyloxypropyl)-1'-(3'"-hydroxypropyl)) -3,3,3',3'-tetramethyl-indodicarbocyanine N⁴-(6-Aminohexyl)-CTP (10 mg), prepared from diaminohexane and CTP by bisulfite catalysis, was dissolved in 200 µL sodium carbonate buffer, pH 9.5. 10 mg of the indodicarbocyanine-NHS ester (see FIG. 2, X=C(CH₃)₂, r=2) was added in 50 µL of DMF. The pH was adjusted to 9.5 and the reaction was allowed to proceed for 2 hours. The product was isolated by NovaPak C18 HPLC (A=0.05 M ammonium phosphate, pH 7.5, B=acetonitrile: 5% for 2 minutes, 5–60% B for 40 minutes). The appropriate peaks were pooled and desalted on a C-18 cartridge. The UV/visible spectrum showed the expected peaks at 646 nm for the dye and 276 nm for an N⁴-derivatized cytosine.

Example 4

(FIG. 5, r=2, X=C(CH₃)₂, R⁴=R⁵=H, R=(CH₂)₃OH, R³=5'-O-triphosphate, linker=DYE-(propyl-O₂C-ethyl-CONH-hexyl)-BASE; sugar=dideoxyribosyl; base=cytosine-N⁴.)

1-3"-((N⁴-6-Amidohexyl-2',3'-dideoxycytidine, 5'-O-triphosphate)-succinoyloxypropyl)-1'-(3'"-hydroxypropyl))-3,3,3',3'-tetramethyl-indodicarbocyanine N⁴-(6-Aminohexyl)-ddCTP, prepared from diaminohexane and 2',3'-dideoxy-CTP by bisulfite catalysis, (14 µmol) was dissolved in 1000 µL of 0.05 M sodium carbonate buffer, pH 9.5. To it was added 8 mg of the indodicarbocyanine-NHS ester (see FIG. 2, X=C(CH₃)², r=2) in 150 µL of DMF and 150 µL water. The pH was adjusted to 9.3 and the reaction was allowed to proceed for 1 hour. The product was isolated by NovaPak C18 HPLC (A=0.05 M ammonium phosphate, pH 7.2, B=acetonitrile: 0% B to 70% B for 40 minutes). The appropriate peaks were pooled and desalted on a C-18 cartridge. The UV/visible spectrum showed the expected peaks at 646 nm for the dye and 276 nm for an N⁴-derivatized cytosine. Yield: 59% of material absorbing at 646 nm, by HPLC analysis. The material was incorporated by a DNA polymerase in a standard sequencing assay, terminating chain extension.

Example 5

(FIG. 5, r=3, X=C(CH₃)₂, R⁴=R⁵=H, R=(CH₂)₃OH, R³=5'-O-triphosphate, linker=DYE-(propyl-O₂C-ethyl-CONH-hexyl)-BASE; sugar=dideoxyribosyl; base=cytosine-N⁴.)

1-3"-((N⁴-6-Amidohexyl-2',3'-dideoxycytidine, 5'-O-triphosphate)-succinoyloxypropyl)-1'-(3'"-hydroxypropyl))-3,3,3',3'-tetramethyl-indotricarbocyanine 1,1"-Bis-(3'-(1-hydroxypropyl))-3,3,3',3'-tetramethyl-indotricarbocyanine)

1-((3'-(1'-Acetoxypropyl))-2,3,3-trimethyl-(3H)-indolinium iodide (2 g) and 0.71 g glutacondialdehyde dianil were dissolved in a mixture of 40 mL acetic anhydride, 10 mL acetic acid, and 1 g of potassium acetate. The solution was refluxed for 20 minutes, at which time the ratio of $A_{740}$ to $A_{280}$ indicated that the reaction was complete. The solvents were evaporated and the residue was dissolved in dichloromethane, extracted three times with aqueous bicarbonate and once with brine, and evaporated. The residue was dissolved in 100 mL of methanol and 100 mL 4 M HCl were added. The reaction was stirred at ambient temperature overnight to complete the hydrolysis of the acetate esters. The solvents were evaporated and the residue was dissolved in dichloromethane, extracted three times with aqueous bicarbonate and once with brine, and evaporated. HPLC confirmed the conversion to the title compound, compared to the diacetyl. UV/vis: $\lambda_{max}$=744 nm maximum (1-(3"'-(1"'-Propyloxysuccinic acid))-1'-(3"-(1"-hydroxypropyl))-3,3,3',3'-tetramethylindotricarbocyanine)

1,1"-Bis-(3'-(1-hydroxypropyl))-3,3,3',3'-tetramethyl-indotricarbocyanine) (0.5 g) was co-evaporated twice with dry pyridine, dissolved in 10 mL of pyridine and treated with 65 mg (1 eq.) of succinic anhydride and 0.055 g 4-dimethylaminopyridine. The reaction was stirred for 4 hours at ambient temperature. Progress was monitored by C-18 HPLC on a 4 µm column at 60% acetonitrile/TEAA, isocratic. After the addition of 1 mL of water, the reaction was evaporated to dryness. The residue was dissolved in 10 mL dichloromethane, extracted with water, and dried. After drying, the organic layer was evaporated to dryness. The residue was dissolved in 10% acetonitrile in 1 M TEAA, pH 7 and purified on a prep HPLC on a NovaPak C18 cartridge with a gradient of 0–70% acetonitrile/0.1 M TEAA, pH 7. Yield: 30 mg.

(1-(3"'-(1"'-Propyloxysuccinic acid, N-hydroxysuccinimide ester))-1'-(3"-(1"-hydroxypropyl))-3,3,3',3'-tetramethylindotricarbocyanine)

(1-(3"'-(1"'-Propyloxysuccinic acid))-1'-(3"-(1"-hydroxypropyl))-3,3,3',3'-tetramethyl-indotricarbocyanine) was dried by co-evaporation twice with dichloromethane, then dissolved in 1 mL of dry dichloromethane and 0.05 mL pyridine. O-Trifluoroacetyl-N-hydroxysuccinimide (0.025 g) was added and the reaction was stirred. The reaction, monitored by C-18 HPLC on a 4 µm column with a gradient of 0–75% acetonitrile/TEAA, pH 7, detected at 648 nm, was over in 5 minutes. Dichloromethane was added to 30 mL and the solution was extracted with water three times, dried, and evaporated. UV/vis: $\lambda_{max}$=744 nm; yield: 34 mg at 80% purity.

1-3"-((N$^4$-6-Amidohexyl-2',3'-dideoxycytidine, 5'-O-triphosphate)-succinoyloxypropyl)-1'-(3'''-hydroxypropyl))-3,3,3',3'-tetramethyl-indotricarbocyanine N$^4$-(6-Aminohexyl)-ddCTP, prepared from diaminohexane and 2',3'-dideoxy-CTP by bisulfite catalysis, (6 mg, 10 $\mu$mol) was dissolved in 700 $\mu$L of 0.07 M sodium carbonate buffer, pH 9.5. To it was added 5 mg of the indotricarbocyanine-NHS ester (FIG. 2, X=C(CH$_3$)$_2$, r=3) in 100 $\mu$L of DMF and 100 $\mu$L water. The pH was adjusted to 9.3 and the reaction was allowed to proceed for 45 minutes. The product was isolated by NovaPak C18 HPLC (A =0.05 M ammonium phosphate, pH 7.2, B=acetonitrile: 0% B to 70% B for 40 minutes). The appropriate peaks were pooled and desalted on a C-18 cartridge. The UV/visible spectrum showed the expected peaks at 744 nm for the dye and 274 nm for an N$^4$-derivatized cytosine. Yield: 1.5 $\mu$mol. The material was incorporated by a DNA polymerase in a standard sequencing assay, terminating chain extension.

Example 6

(FIG. 5, r=3, X=C(CH$_3$)$^2$, R$^4$=R$^5$=H, R=(CH$_2$)$_3$OH, R$^3$=5'-O-triphosphate, linker=DYE-(propyl-O$_2$C-ethyl-CONH-hexyl)-BASE; sugar=deoxyribosyl; base=cytosine-N$^4$.)

1-3"-((N$^4$-6-Amidohexyl-2'-deoxycytidine, 5'-O-triphosphate)-succinoyloxypropyl)-1'-(3'''-hydroxypropyl))-3,3,3',3'-tetramethylindotricarbocyanine N$^4$-(6-Aminohexyl)-dCTP, prepared from diaminohexane and 2'-deoxy-CTP by bisulfite catalysis, (1 mg) was dissolved in 1000 $\mu$L of 0.1 M sodium carbonate buffer, pH 9.5. To it was added 1 mg of the indotricarbocyanine-NHS ester (FIG. 3, X=C(CH$_3$)$_2$, r=3) in 50 $\mu$L of DMF and 50 $\mu$L water. The pH was adjusted to 9.3 and the reaction was allowed to proceed for 45 minutes. The product was isolated by Nova-Pak C18 HPLC (A=0.05 M ammonium phosphate, pH 7.2, B=acetonitrile: 0% B to 70% B for 40 minutes). The appropriate peaks were pooled and desalted on a C-18 cartridge. The UV/visible spectrum showed the expected peaks at 744 nm for the dye and 274 nm for an N$^4$-derivatized cytosine. Yield: 50% of material absorbing at 744 nm is product, by HPLC analysis.

Example 7

(FIG. 5, r=3, X=C(CH$_3$)$_2$, R$^4$=R$^5$=H, R=(CH$_2$)$_3$OH, R$^3$=5'-O-triphosphate, linker=DYE-(propyl-O$_2$C-ethyl-CONH-hexyl)-BASE; sugar=dideoxyribosyl; base= adenine-N$^6$.)

1-3"-((N$^6$-6-Amidohexyl-2',3'-dideoxyadenosine, 5'-O-triphosphate)-succinoyloxypropyl)-1'-(3'''-hydroxypropyl))-3,3,3',3'-tetramethyl-indotricarbocyanine N$^6$-(6-Aminohexyl)-ddATP, prepared by reaction of diaminohexane and 6-chloropurine-2',3'-dideoxyriboside-5'-O-triphosphate (10 $\mu$mol) was dissolved in 500 $\mu$L of 0.08 M sodium carbonate buffer, pH 9.5. To it was added 3 mg of the indotricarbocyanine-NHS ester (FIG. 3, X=C(CH$_3$)$_2$, r=3) in 75 $\mu$L of DMF and 75 $\mu$L water. The pH was adjusted to 9.3 and the reaction was allowed to proceed for 2 hours. The product was isolated by NovaPak C18 HPLC (A=0.05 M ammonium phosphate, pH 7.2, B=acetonitrile: 0% B to 70% B for 40 minutes). The appropriate peaks were pooled, the acetonitrile evaporated, and the product stored in ammonium phosphate solution. The UV/visible spectrum showed the expected peaks at 746 nm for the dye and 271 nm for an N$^6$-substituted adenine. Yield: 48 nmol.

Example 8

(FIG. 5, r=1, X=C(CH$_3$)$_2$, R$^4$=R$^5$=H, R=(CH$_2$)$_3$OH, R$^3$=5'-O-triphosphate, linker=DYE-(propyl-O$_2$C-ethyl-CONH-propynyl)-BASE; sugar=dideoxyribosyl; base=7-deazaguanine-C$^7$.)

1-3"-((7-(3-Amidopropynyl-2',3'-dideoxy-7-deazaguanosine, 5'-O-triphosphate)-succinoyloxypropyl)-1'-(3'''-hydroxypropyl))-3,3,3',3'-tetramethyl-indomonocarbocyanine (1-(3'''-(1'''-Propyloxysuccinic acid))-1'-(3"-(1"-(p-methoxytrityl)oxypropyl))-3,3,3',3'-tetramethyl-indomonocarbocyanine)

The mono MMTr intermediate from the preparation of the IMC amidite (0.2 g) was co-evaporated twice with dry pyridine, dissolved in 2 mL of pyridine, and treated with 0.077 g succinic anhydride and 0.022 g 4-dimethylaminopyridine. The reaction was stirred for 2 hours at ambient temperature. Progress was monitored by C-18 HPLC on a 3 $\mu$m column at 60% acetonitrile/TEAA, isocratic. After the addition of 0.2 mL of water, the reaction was evaporated to dryness. The residue was dissolved in dichloromethane and was extracted with aqueous bicarbonate and brine. After drying, the organic layer was evaporated to dryness. UV/vis: : $\lambda_{max}$=550 nm.

(1-(3'''-(1'''-Propyloxysuccinic acid))-1'-(3"-(1"-hydroxypropyl))-3,3,3',3'-tetramethyl-indomonocarbocyanine)

The material from the previous reaction was dissolved in 10 mL of 80% acetic acid in water. After three hours at ambient temperature, the detritylation was complete, with no hydrolysis of the succinate ester. Progress was monitored by C-18 HPLC. The solution was evaporated and the residue dissolved in dichloromethane, extracted with aqueous bicarbonate three times, and brine. The solution was dried and evaporated. Yield 130 mg. Uv/vis: $\lambda_{max}$=550 nm.

(1-(3'''-(1'''-Propyloxysuccinic acid, N-hydroxysuccinimide ester))-1'-(3"-(1"-hydroxypropyl))-3,3,3',3'-tetramethyl-indomonocarbocyanine)

The dry solid co-evaporated twice with dry pyridine, and was dissolved in 2 mL of dry dichloromethane, followed by 0.1 mL pyridine and 0.2 g (~3 eq) of O-trifluoroacetyl-N-hydroxysuccinimide. The reaction, monitored by C-18 HPLC, was over in 5 minutes. Dichloromethane was added and the solution was extracted with water three times, dried, and evaporated. HPLC analysis (10–90% acetonitrile in 0.1 M TEAA, pH 7) showed the material to be about 85% pure. Yield 180 mg. UV/vis: $\lambda_{max}$=550 nm.

1-3"-((7-(3-Amidopropynyl-2',3'-dideoxy-7-deazaguanosine, 5'-O-triphosphate)-succinoyloxypropyl)-1'-(3'''-hydroxypropyl))-3,3,3',3'-tetramethyl-indomonocarbocyanine 7-(3-Aminopropynyl)-7-deaza-2',3'-ddGTP (0.25 $\mu$mol), obtained from NEN/DuPont, was dissolved in 0.1 M aqueous carbonate buffer, pH 9.5. (1-(3'''-(1'''-Propyloxysuccinic acid, N-hydroxysuccinimide ester))-1'-(3"-(1"-hydroxypropyl))-3,3,3',3'-tetramethyl-indomonocarbocyanine) (1 mg) was added in 50 $\mu$L each of DMF and water. The pH was adjusted to 9.2. After 1 hour the reaction was quenched by the addition of NaH$_2$PO$_4$ to pH 6.7. The product was purified on C-18 HPLC with acetonitrile and ammonium phosphate, pH 6. The appropriate peaks were pooled, the acetonitrile evaporated, and the product stored in ammonium phosphate solution. Yield: 29 nmol. UV/vis: $\lambda_{max}$=550 nm.

Example 9

(FIG. 5, r=1, X=C(CH$_3$)$_2$, R$^4$=R$^5$=H, R=(CH$_2$)$_3$OH, R$^3$=5'-O-triphosphate, linker=DYE-(propyl-O$_2$C-ethyl-CONH-hexyl)-BASE; sugar deoxyribosyl; base=cytosine-N$^4$.)

1-3"-((N$^4$-(6-Amidohexyl-2'-deoxycytidine, 5'-O-triphosphate)-succinoyloxypropyl)-1'-(3'"-hydroxypropyl))-3,3,3',3'-tetramethyl-indomonocarbocyanine N$^4$-(6-Aminohexyl)-dCTP (1 mg), prepared from diaminohexane and 2'-deoxy-CTP by bisulfite catalysis, was dissolved in 0.1 M aqueous carbonate buffer, pH 9.5. (1-(3-(1'"-propyloxysuccinic acid, N-hydroxysuccinimide ester))-1'-(3"-(1"-hydroxypropyl))-3,3,3',3'-tetramethyl-indomonocarbocyanine) (1 mg) was added in 50 µL each of DMF and water. The pH was adjusted to 9.2. After 1 hour the presence of the product was confirmed by HPLC by comparison to similar compounds. UV/vis: $\lambda_{max}$=550 nm.

Example 10

(FIG. 5, r=1, X=O, R$^4$=R$^5$=H, R=(CH$_2$)$_3$OH, R$^3$=5'-O-triphosphate, linker=DYE-(propyl-O$_2$C-ethyl-CONH-hexyl)-BASE; sugar=dideoxyribosyl; base=cytosine-N$^4$.)

1-3"-((N$^3$-6-Amidohexyl-2',3'-dideoxycytidine, 5'-O-triphosphate)-succinoyloxypropyl)-1'-(3'"-hydroxypropyl))-benzoxazolmonocarbocyanine 1-((3'-(1'-Acetoxypropyl))-benzoxazolium iodide 2-Methylbenzoxaole (7.0 g 0.053 mol) and 13.2 g (0.03 mol) of 3-iodopropyl acetate were heated together at 100–110° C. for 16 hours. The mixture was crystallized to a granular powder by trituration in ethyl acetate. It was filtered and dried by washing with ether. Yield: 15.1 g.

1,1"-Bis-(3"-(1-acetoxypropyl))-benzoxazolmonocarbocyanine 1-((3'-(1'-Acetoxypropyl))-benzoxazolium iodide (5 g, 0.014 mol) and 4.5 g of triethylorthoformate were dissolved in 100 mL dry pyridine. The solution was refluxed for three hours. The solvents were evaporated and the residue crystallized from ethyl acetate. Yield: 4.9 g. UV/vis: $\lambda_{max}$=484 nm.

(1-(3"-(1"-acetoxypropyl)-1"-(3'"-(1'"-hydroxypropyl))-benzoxazolmonocarbocyanine 1-((3'-(1'-Acetoxypropyl))-benzoxazolium iodide (1 g) was stirred in a mixture of 20 mL of 4N HCl and 20 mL methanol for 1 hour, then was rotovaped to dryness. The residue was dissolved in dichloromethane and extracted with water. The water was back-extracted three times with dichloromethane. The organic layers were combined, dried, and evaporated. The material was purified by C18 prep HPLC on a 25×200 mm Novapak cartridge using a 10–65% acetonitrile/TEAA gradient. The fractions enriched in the mono-acetyl derivative were pooled and evaporated to dryness.

(1-(3'"-(1"'-Propyloxysuccinic acid))-1'-(3'"-(1"'-acetoxypropyl))-benzoxazolmonocarbocyanine The mono-acetyl derivative (175 mg) was dried by co-evaporation three times with dry acetonitrile and dissolved in 1 mL of dry pyridine. Succinic anhydride and DMAP were added and the reaction proceeded for 2 hours. The reaction was quenched with 1 mL water and the product purified by C18 prep HPLC on a 25×100 mm Novapak cartridge using a 0–80% acetonitrile/TEAA gradient. Yield: 22 mg.

(1-(3'"-(1'"-Propyloxysuccinic acid N-hydroxysuccinimide ester))-1'-(3"'-(1"'-acetoxypropyl))-benzoxazolmonocarbocyanine The succinate derivative (22 mg) was dried by co-evaporation two times with dry pyridine and dissolved in 1 mL of dry dichloromethane with 50 µL of dry pyridine. O-Trifluoroacetyl-N-hydroxysuccinimide (100 mg) was added. After 5 minutes the reaction was diluted with 5 mL dichloromethane and extracted twice with water. The dichloromethane was dried and evaporated to yield 20 mg of activated ester.

1-3"-(N$^4$-6-Amidohexyl-2',3'-dideoxycytidine,5'-O-triphosphate)-succinoyloxypropyl)-1'-(3'"-hydroxypropyl))-benzoxazolmonocarbocyanine The activated ester (2 mg) was dissolved in 200 µL 50% DMF/water and 4 µmol of 6-aminohexyl-ddCTP in 500 µL 0.1 M carbonate buffer, pH 9 was added. After 45 minutes the reaction was terminated. The product was purified by C18 HPLC (3.9×150 mm Novapak, 0–75% acetonitrile/ammonium phosphate, pH 6. Yield: 584 nmol. UV/vis 484, 272 nm.

The material was incorporated by a DNA polymerase in a standard sequencing assay, terminating chain extension.

REFERENCES

1. Hamer, "Cyanine Dyes and Related Compounds," Interscience Publishers, pp. 86–350, 1964.

2. Sturmer et al., "Sensitizing and Desensitizing Dyes," Special Topics in Heterocyclic Chemistry, Ch. 8, pp. 194–197, 1977.

3. (a) Southwick, Ernst, Tauriello, Parker, Mujumdar, Mujumdar, Clever, and Waggoner, "Cyanine Dye Labeling Reagents—Carboxymethylindocyanine Succinimidyl Esters," Cytometry 11:418–430, 1990.

(b) Yu, Ernst, Wagner, and Waggoner, "Sensitive Detection of RNAs in Single Cells by Flow Cytometry," Nuc. Acids Res. 20:83–88, 1992.

(c) Galbraith, Wagner, Chao, Abaza, Ernst, Nederlof, Hartsock, Taylor, and Waggoner, Cytometry, 12:579–596, 1991.

(d) Ernst, Gupta, Mujumdar, and Waggoner, Cytometry, 10:3–10, 1989.

4. (a) Mujumdar, Ernst, Mujumdar, Lewis, and Waggoner, "Cyanine Dye Labeling Reagents: Sulfoindocyanine Succinimidyl Esters," Bioconjugate Chem. 4:105–111, 1993.

(b) Mujumdar, Mujumdar, Grant, and Waggoner, "Cyanine Dye Labeling Reagents: Sulfobenz(e)indocyanine Succinimidyl Esters," Bioconjugate Chem. 7:356–362, 1996.

(c) U.S. Pat. No. 4,981,977; January 1991, Southwick and Waggoner.

(d) U.S. Pat. No. 5,268,486; December 1993, Waggoner, et al.

(e) U.S. Pat. No. 5,486,616; January 1996, Waggoner, et al.

(f) U.S. Pat. No. 5,569,587; October 1996, Waggoner.

(g) U.S. Pat. No. 5,569,766; October 1996, Waggoner, et al.

5. (a) U.S. Pat. No. 5,047,519; September 1991, Hobbs and Cucozza.

(b) U.S. Pat. No. 5,151,507; September 1992, Hobbs and Trainor.

(c) U.S. Pat. No. 5,242,796; September 1993, Prober, et al.

(d) U.S. Pat. No. 5,332,666; July 1994, Prober, et al.
(e) U.S. Pat. No. 5,558,991; September 1996, Trainor.
(f) U.S. Pat. No. 4,828,979; May 1989, Klevan, et al.
(g) PCT WO 95/04747, Mühlegger, et al.
(h) PCT/EP92/01756, Ansorge, et al.

6. (a) U.S. Pat. No. 4,711,955; December 1987, Ward, et al.
(b) U.S. Pat. No. 5,328,824; July 1994; Ward, et al.
(c) U.S. Pat. No. 5,449,767; September 1995, Ward, et al.
(d) U.S. Pat. No. 5,476,928; December 1995, Ward, et al.
(e) U.S. Pat. No. 5,241,060; August 1993, Englehart, et al.

7. (a) Yu, Chao, Patek, Mujumdar, Mujumdar, and Waggoner, "Cyanine Dye dUTP Analogs For Enzymatic Labeling Of DNA Probes," *Nuc. Acids Res.* 22:3226–3232, 1994.
(b) Amersham Life Science Catalogue, 1996.

8. Johnson, Zhang, and Bergstrom, "The synthesis and stability of oligodeoxyribonucleotides containing deoxyadenosine mimic 1-(2'-deoxy-β-D-ribofuranosyl) rinidazole-4-carboxamide," *Nuc. Acids Res.* 25:559–567, 1997.

We claim:

1. A chemical compound of the following formula:

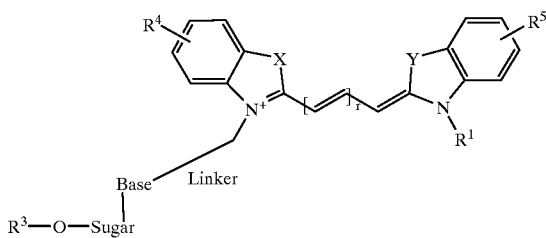

wherein:

$R^1$ is selected from the group consisting of alkyl and aralkyl groups;

$R^3$ is selected from the group consisting of H, $PO_3^{-2}$; $P_2O_6^{-3}$; $P_3O_9^{-4}$; α-thio phosphates; and $\alpha BH_3^-$ phosphates;

$R^4$ is selected from the group consisting of H, lower alkyl, acyl, $(CH_2)_pCOO(CH_2)_qCH_3$ wherein p is an integer from 0 to 4 and q is an integer from 0 to 4, and 5,6-butadienyl, 6,7-butadienyl or 7,8-butadienyl;

$R^5$ is selected from the group consisting of H, lower alkyl, acyl, and $(CH_2)_pCOO(CH_2)_qCH_3$ wherein p is an integer from 0 to 4 and q is an integer from 0 to 4 and 5,6; 6,7; or 7,8-butadienyl;

r is 1, 2, or 3;

X or Y are selected from the group consisting of O, S, $C(R^6)_2$, and $N(R^6)$, wherein $R^6$ is $CH_3$ or a lower alkyl;

$R^3$—O-Sugar-Base is a nucleoside or nucleotide, linker is a chain of carbon, oxygen, nitrogen or sulfur atoms that connects N to Base, Base is selected from the group consisting of uracil, thymine, cytosine, guanine, 7-deazaguanine, hypoxanthine, 7-deazahypoxanthine, adenine, or 7-deazaadenine, 2,6-diaminopurine and other nitrogen-heterocycle bases, sugar is selected from the group consisting of ribosyl, 2'-deoxyribosyl, 3'-deoxyribosyl, or 2',3'-dideoxyribosyl or 2'-oxabutyl.

2. The compound of claim 1 wherein $R^1$ is selected from the group consisting of substituted alkyl chains, wherein the substitution is $OR^2$, $COOR^2$, $NR^2R^2$, or $SR^2$, wherein $R^2$ is H, a removable protecting group or a lower alkyl group.

3. The compound of claim 2 wherein $R^2$ is selected from the group consisting of H, a removable protecting group, or a lower alkyl group.

4. The compound of claim 1 wherein $R^1$ is $(CH_2)_3OH$.

5. The compound of claim 1 wherein $R^1$ is selected from the group consisting of $(CH_2)_5COOH$, $(CH_2)_3NH_2$ and $C_2H_5$.

6. The compound of claim 1 wherein $R^3$ is selected from the group consisting of $PO_3^{-2}$, $P_2O_6^{-3}$ and $P_3O_9^{-4}$.

7. The compound of claim 1 wherein the linker is selected from the group consisting of propyl-O—$PO_2$—O-hexyl, propyl-$O_2$C-ethyl-CO, propyl-$O_2$C-ethyl-CONH-hexyl, and propyl-$O_2$C-ethyl-CONH-propynyl.

8. The compound of claim 1 wherein the linker is between 3 and 25 atoms in length.

9. The compound of claim 1 wherein X and Y are $C(CH_3)_2$.

10. The compound of claim 1 wherein the nucleotide or nucleoside formed by $R^3$—O-Sugar-Base is selected from the group consisting of IDC-rCTP, IDC-dCTP, IDC-ddCTP, ITC-ddCTP, ITC-ddATP, IDC-dATP, IMC-c7-ddGTP, and OMC-ddCTP.

11. The compound of claim 1 wherein $R^3$ is selected from the group consisting of $PSO_2^{-2}$; $P_2SO_5^{-3}$; and $P_3SO_8^{-4}$.

12. The compound of claim 1 wherein $R^3$ is selected from the group consisting of $P(BH_3)O_2^{-2}$, $P_2(BH_3)O_5^{-3}$, and $P_3(BH_3)O_8^{-4}$.

13. A method of labeling a nucleic acid molecule comprising the step of incorporating the compound of claim 1 into a nucleic acid chain.

14. The method of claim 13 further comprising the step of determining the nucleic acid sequence of the molecule.

* * * * *